United States Patent
Luebke

(10) Patent No.: US 8,062,033 B2
(45) Date of Patent: Nov. 22, 2011

(54) DENTAL AND MEDICAL INSTRUMENTS COMPRISING TITANIUM

(75) Inventor: Neill Hamilton Luebke, Brookfield, WI (US)

(73) Assignee: Gold Standard Instruments, LLC, Brookfield, WI (US)

( * ) Notice: Subject to any disclaimer, the term of this patent is extended or adjusted under 35 U.S.C. 154(b) by 0 days.

(21) Appl. No.: 11/628,933

(22) PCT Filed: Jun. 7, 2005

(86) PCT No.: PCT/US2005/019947
§ 371 (c)(1),
(2), (4) Date: Dec. 7, 2006

(87) PCT Pub. No.: WO2005/122942
PCT Pub. Date: Dec. 29, 2005

(65) Prior Publication Data
US 2008/0032260 A1 Feb. 7, 2008

Related U.S. Application Data

(60) Provisional application No. 60/578,091, filed on Jun. 8, 2004.

(51) Int. Cl.
*A61C 5/02* (2006.01)
(52) U.S. Cl. ...................................................... 433/102
(58) Field of Classification Search .................. 433/102, 433/224; 29/896.1, 896.11; 148/402, 421, 148/426, 669
See application file for complete search history.

(56) References Cited

U.S. PATENT DOCUMENTS

| | | | | |
|---|---|---|---|---|
| 4,490,112 A | * | 12/1984 | Tanaka et al. | 433/20 |
| 5,080,584 A | * | 1/1992 | Karabin | 433/20 |
| 5,653,590 A | * | 8/1997 | Heath et al. | 433/102 |
| 5,775,902 A | * | 7/1998 | Matsutani et al. | 433/102 |
| 6,206,695 B1 | * | 3/2001 | Wong et al. | 433/102 |
| 6,375,458 B1 | * | 4/2002 | Moorleghem et al. | 433/2 |
| 6,422,865 B1 | * | 7/2002 | Fischer | 433/81 |
| 6,428,634 B1 | * | 8/2002 | Besselink et al. | 148/421 |
| 6,431,863 B1 | * | 8/2002 | Sachdeva et al. | 433/102 |
| 6,783,438 B2 | | 8/2004 | Aloise et al. | |
| 7,137,815 B2 | * | 11/2006 | Matsutani et al. | 433/102 |
| 7,175,655 B1 | | 2/2007 | Molaci | |
| 2002/0191878 A1 | * | 12/2002 | Ueda et al. | 384/492 |
| 2004/0121283 A1 | * | 6/2004 | Mason | 433/102 |
| 2004/0171333 A1 | | 9/2004 | Aloise et al. | |
| 2006/0014480 A1 | | 1/2006 | Aloise et al. | |

OTHER PUBLICATIONS

International Search Report corresponding to PCT/US2005/019947, under date of mailing of Nov. 10, 2005.

* cited by examiner

*Primary Examiner* — Todd Manahan
*Assistant Examiner* — Matthew Nelson
(74) *Attorney, Agent, or Firm* — Quarles & Brady LLP

(57) ABSTRACT

Endodontic instruments for use in performing root canal therapy on a tooth are disclosed. In one form, the instruments include an elongate shank having a cutting edge extending from a distal end of the shank along an axial length of the shank. The shank comprises a titanium alloy, and the shank is prepared by heat-treating the shank at a temperature above 25° C. in an atmosphere consisting essentially of a gas unreactive with the shank. In another form, the endodontic instruments have an elongate shank having a cutting edge extending from a distal end of the shank along an axial length of the shank. The shank consists essentially of a titanium alloy selected from alpha-titanium alloys, beta-titanium alloys, and alpha-beta-titanium alloys. The instruments solve the problems encountered when cleaning and enlarging a curved root canal.

18 Claims, 7 Drawing Sheets

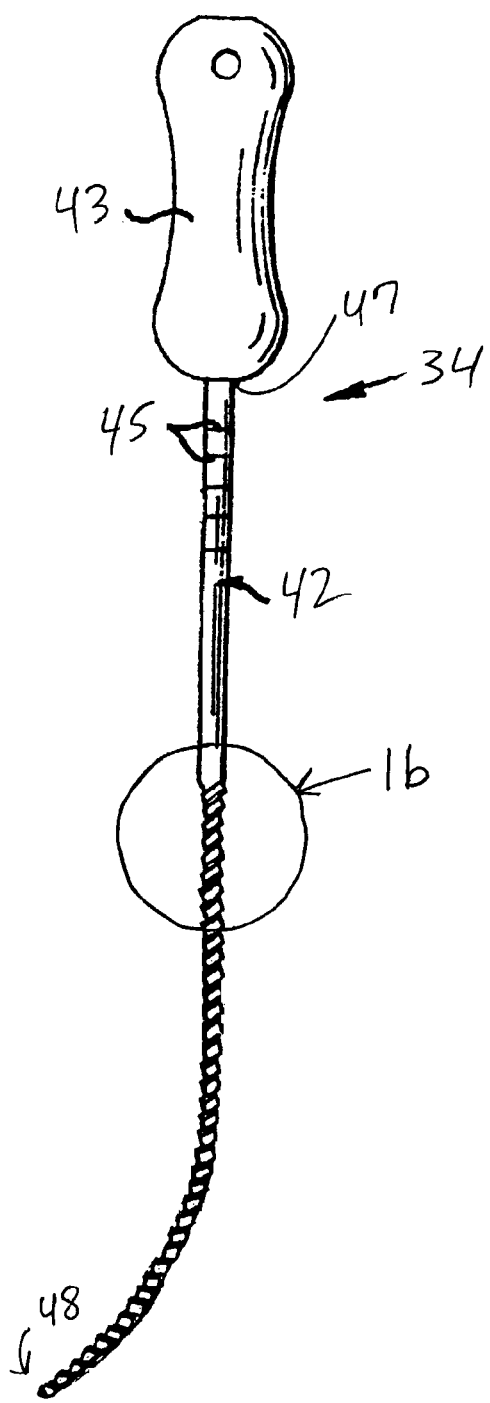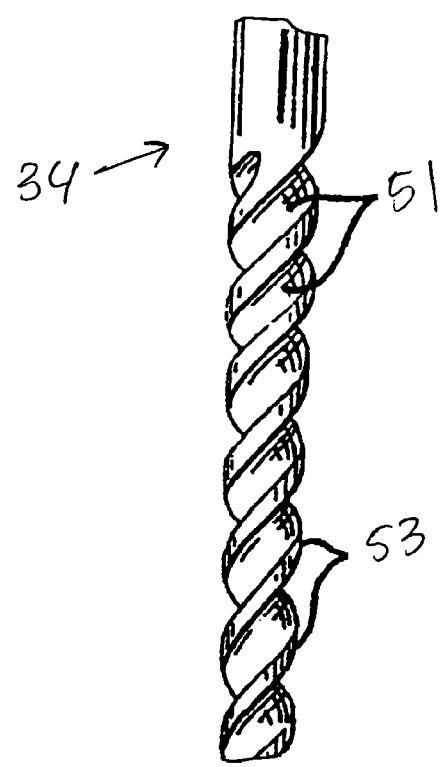
Fig. 1a
Fig. 1b

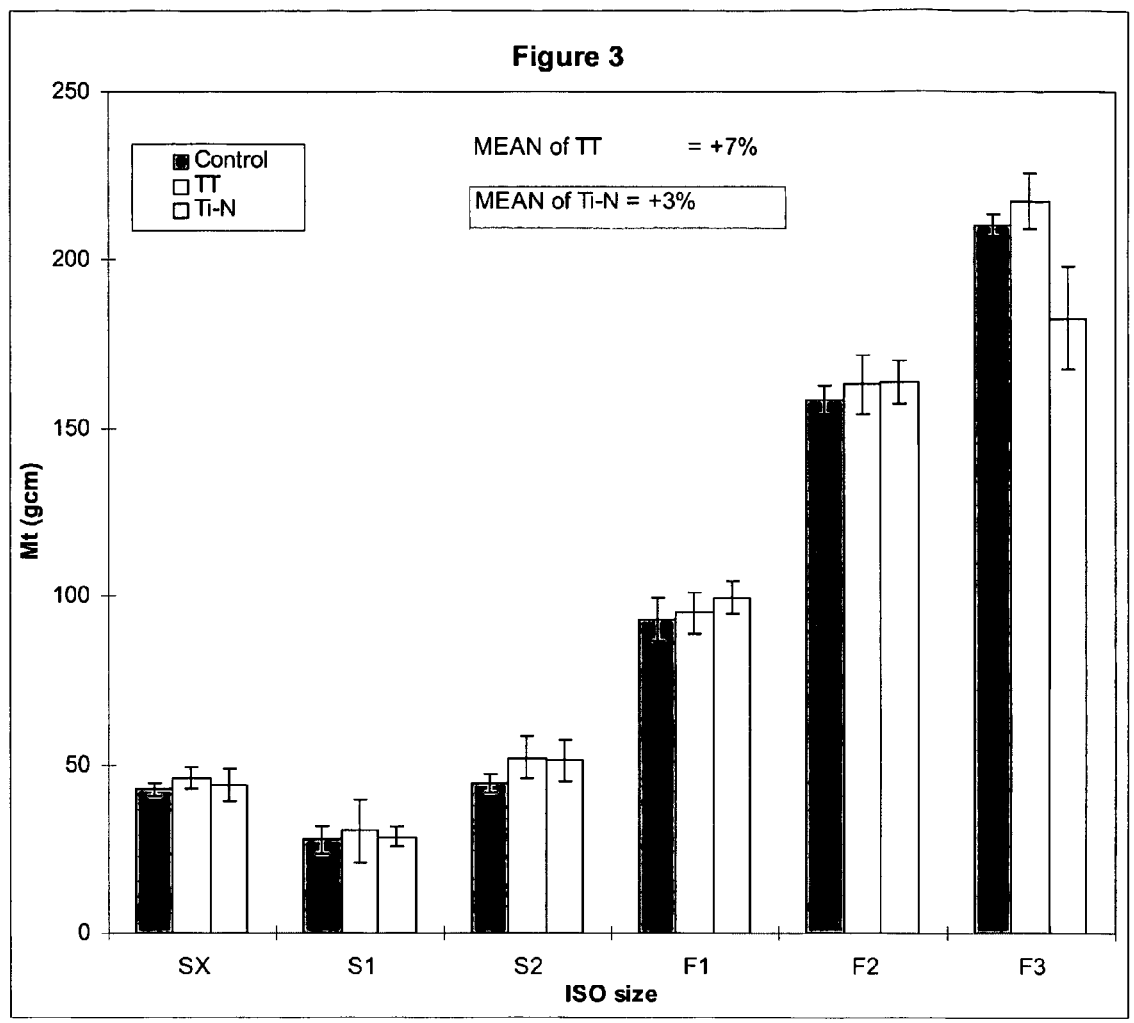

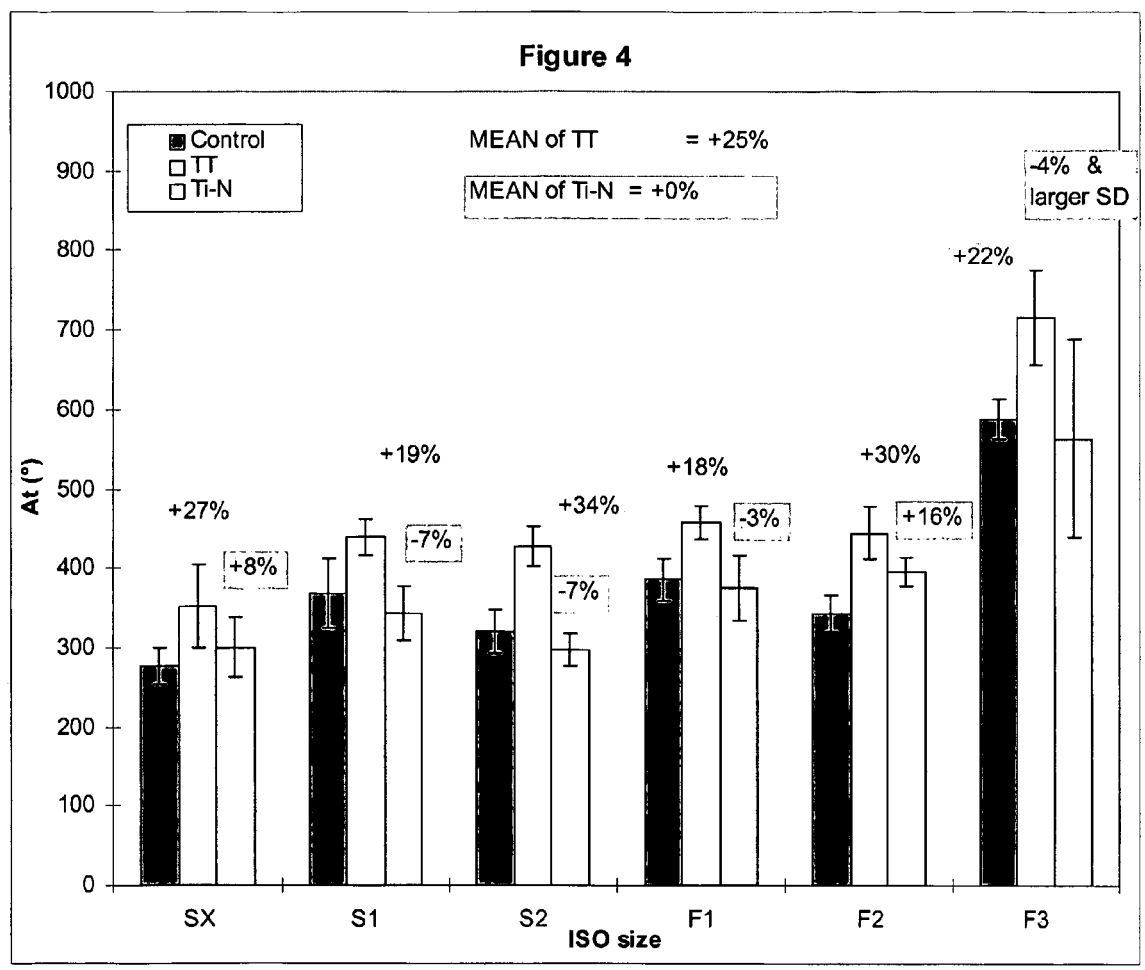

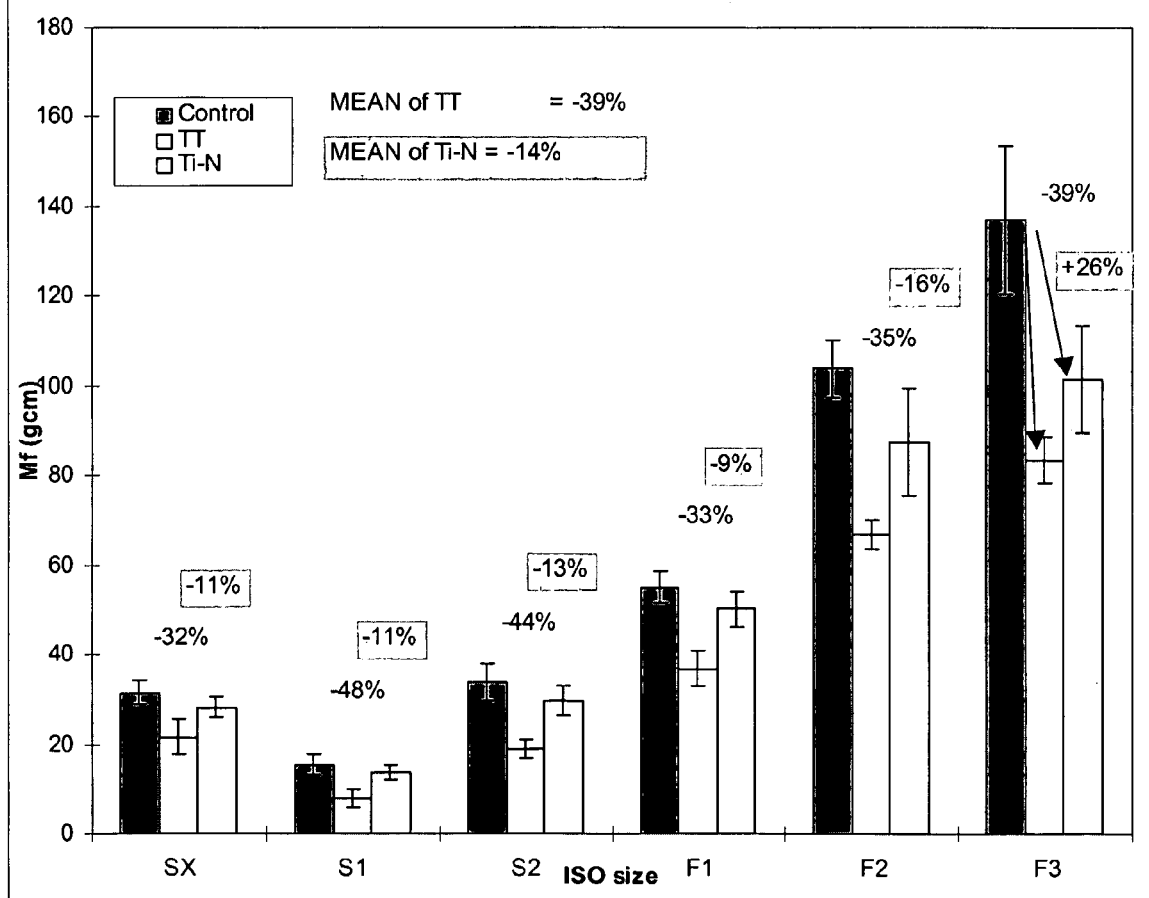

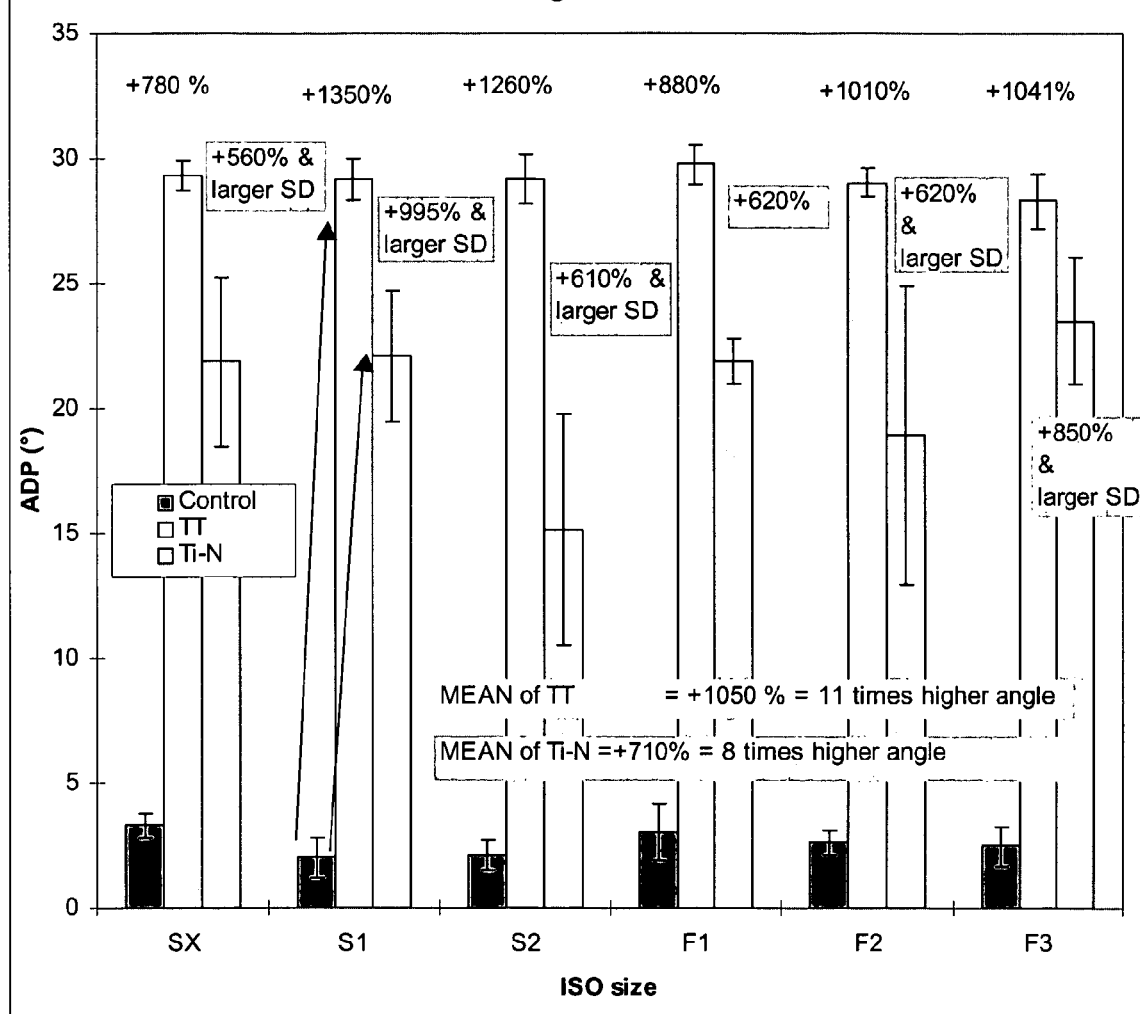

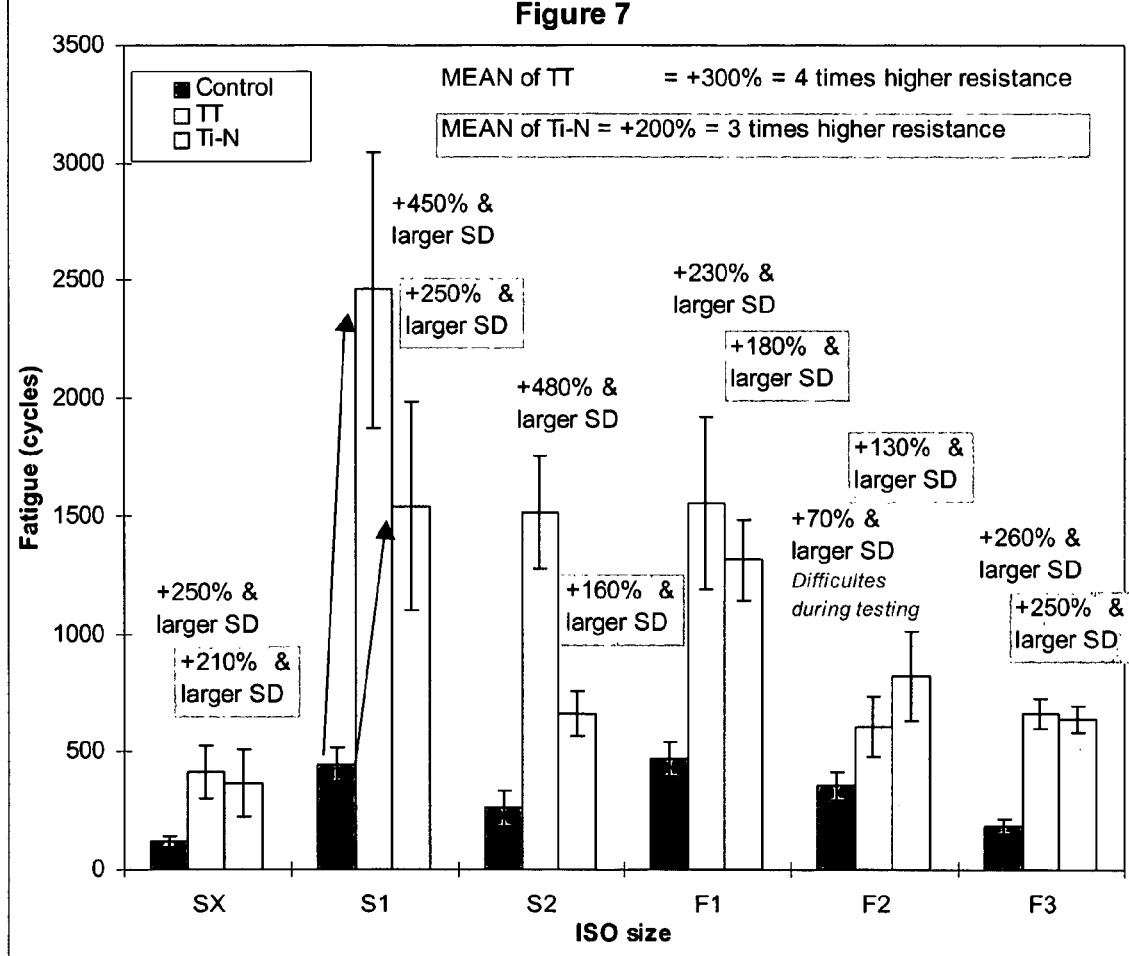

DENTAL AND MEDICAL INSTRUMENTS COMPRISING TITANIUM

CROSS-REFERENCES TO RELATED APPLICATIONS

This application claims priority from U.S. Provisional Patent Application No. 60/578,091 filed Jun. 8, 2004.

STATEMENT REGARDING FEDERALLY SPONSORED RESEARCH

Not Applicable.

BACKGROUND OF THE INVENTION

1. Field of the Invention

The invention relates to instruments used in medicine and dentistry. More particularly, the invention relates to medical and dental instruments such as drills, burs and files, and to endodontic instruments such as drills, burs and files used by dentists.

2. Description of the Related Art

Endodontics or root canal therapy is the branch of dentistry that deals with diseases of the dental pulp and associated tissues. One aspect of endodontics comprises the treatment of infected root canals by removal of diseased pulp tissues and subsequent filling.

FIG. 1 shows a representation of a tooth to provide background. Root canal therapy is generally indicated for teeth having sound external structures but having diseased, dead or dying pulp tissues. Such teeth will generally possess intact enamel 10 and dentin 12, and will be satisfactorily engaged with the bony tissue 20, by among other things, healthy periodontal ligaments 18. In such teeth, the pulp tissue 14, and excised portions of the root 16, should be replaced by a biocompatible substitute. FIG. 1 also shows the apical foramen 22 through which blood and nerves pass to support the pulp tissues.

One method for the preparation of a root canal for filling is represented by FIGS. 2a-2e. A tooth having a basically sound outer structure 24 but diseased pulp 26, is cut with conventional or coated dental drill 28 creating a coronal access opening 30. A broach is used for gross removal of pulp material 26 from the root canal through the coronal access opening 30. The void 32 formed is enlarged as in FIG. 2d with file 34, to result in a fully excavated cavity 36. Debris is removed from this cavity by flushing and the cavity cleansed to remove all diseased tissue. The excavated canal is then ready for filling.

During this procedure, small endodontic instruments (e.g., file 34) are utilized to clean and enlarge the long narrow tapered root canals. While most files perform entirely satisfactorily when cleaning and enlarging a straight root canal, problems have been encountered when using certain files to clean and enlarge a curved root canal. As will be understood by those skilled in the art, a very large portion of the root canals encountered by a practicing dentist and/or endodontist are of the curved variety, and thus this problem is a significant one for the profession.

When performing an operation on a curved root canal with a smaller diameter file, the file can easily be inserted into the curved canal and will easily bend to fit the curved shape of the canal due to the flexibility of the small diameter file. In FIG. 1a, there is shown the file 34 of FIG. 2d in a bent position. The file 34 has a shank 42 mounted at its proximate end 47 to a handle 43. The shank 42 may include calibrated depth markings 45 and further includes a distal end 48. The shank 42 includes two continuous helical flutes 51 as shown in FIG. 1b that extend along its lower portion. The flutes 51 define a cutting edge. A helical land 53 is positioned between axially adjacent flutes as shown in FIG. 1b.

While file 34 can easily bend to fit the curved shape of a canal due to the flexibility of the small diameter shank 42, with increasingly larger sizes of files, the file becomes significantly less flexible and becomes more and more difficult to insert through the curved portion of the canal. In some cases, the relatively inflexible file will cut only on the inside of the curve and will not cut on the outside of the curvature of the root canal. Thus, the problems, which occur during the therapy of a root canal, are often the result of the basic stiffness of the files, particularly with the respect to the instruments of larger diameter.

Various solutions have been proposed to limit the problems encountered when cleaning and enlarging a curved root canal with a file. For example, U.S. Pat. No. 4,443,193 describes a shaped endodontic instrument that is said to solve this problem. U.S. Pat. No. 5,380,200 describes an endodontic instrument having an inner core and an outer shell wherein one of the cores or shell is a nickel-titanium alloy and the other core or shell is selected from stainless steel, titanium alpha alloy, titanium beta alloy, and titanium alpha beta alloy. (For background on beta-titanium, see U.S. Pat. Nos. 4,197,643; 4,892,479; 4,952,236; 5,156,807; 5,232,361; 5,264,055; 5,358,586; 5,947,723; 6,132,209; and 6,258,182.) U.S. Pat. No. 5,464,362 describes an endodontic instrument of a titanium alloy that is machined under certain specific operating parameters to produce an instrument having high flexibility, high resistance to torsion breakage, and sharp cutting edges. U.S. Pat. No. 6,315,558 proposes the use of superelastic alloys such as nickel-titanium that can withstand several times more strain than conventional materials without becoming plastically deformed. This property is termed shape memory, which allows the superelastic alloy to revert back to a straight configuration even after clinical use, testing or fracture (separation).

In spite of the aforementioned advances, there remains a need for medical and dental instruments, and particularly endodontic instruments, such as drills, burs and files, that have high flexibility, have high resistance to torsion breakage, maintain shape upon fracture, can withstand increased strain, and can hold sharp cutting edges.

SUMMARY OF THE INVENTION

The present invention overcomes the problems encountered when cleaning and enlarging a curved root canal. In one aspect, the invention provides an endodontic instrument for use in performing root canal therapy on a tooth. The instrument includes an elongate shank having a cutting edge extending from a distal end of the shank along an axial length of the shank. The shank comprises a titanium alloy, and the shank is prepared by heat-treating the shank at a temperature above 25° C. in an atmosphere consisting essentially of a gas unreactive with the shank. The shank has high flexibility, high resistance to torsion breakage, maintains shape upon fracture, can withstand increased strain, and can hold sharp cutting edges. Thus, it solves the problems encountered when cleaning and enlarging a curved root canal.

In another aspect, the invention provides an endodontic instrument for use in performing root canal therapy on a tooth. The instrument has an elongate shank having a cutting edge extending from a distal end of the shank along an axial length of the shank. The shank consists essentially of a titanium alloy selected from alpha-titanium alloys, beta-titanium alloys, and alpha-beta-titanium alloys. The shank avoids the use of complex two material systems that are expensive to produce and are prone to delamination of the materials. This version of the invention also solves the problems encountered when cleaning and enlarging a curved root canal.

These and other features, aspects, and advantages of the present invention will become better understood upon consideration of the following detailed description, drawings, and appended claims.

BRIEF DESCRIPTION OF THE DRAWINGS

FIG. 1a is a side elevational view of an endodontic instrument.

FIG. 1b is a partial detailed view of the shank of the endodontic instrument shown in FIG. 1a.

FIG. 3 is a graph showing the results of a study of torsion ($M_t$) reported in g·cm performed in accordance with "ISO Standard 3630-1 Dentistry—Root-canal instruments—Part 1: General requirements" and "ANSI/ADA Specification No. 28, Endodontic files and reamers" for untreated (Control) files, heat-treated files (TT), and titanium nitride coated files (Ti—N).

FIG. 4 is a graph showing the results of a study of torsion ($A_t$) reported in degrees of deflection performed in accordance with "ISO Standard 3630-1 Dentistry—Root-canal instruments—Part 1: General requirements" and "ANSI/ADA Specification No. 28, Endodontic files and reamers" for untreated (Control) files, heat-treated files (TT), and titanium nitride coated files (Ti—N).

FIG. 5 is a graph showing the results of a study of maximum torque at 45° of flexion (Mf) reported in g-cm performed in accordance with "ISO Standard 3630-1 Dentistry—Root-canal instruments—Part 1: General requirements" and "ANSI/ADA Specification No. 28, Endodontic files and reamers" for untreated (Control) files, heat-treated files (TT), and titanium nitride coated files (Ti—N).

FIG. 6 is a graph showing the results of a study of angle of permanent deformation after the flexion test (ADP) reported in degrees of deflection performed in accordance with "ISO Standard 3630-1 Dentistry—Root-canal instruments—Part 1: General requirements" and "ANSI/ADA Specification No. 28, Endodontic files and reamers" for untreated (Control) files, heat-treated files (TT), and titanium nitride coated files (Ti—N).

FIG. 7 is a graph showing the results of a study of fatigue reported in cycles (revolutions) to failure for untreated (Control) files, heat-treated files (TT), and titanium nitride coated files (Ti—N). This study was performed in accordance with the "ISO Standard 3630-2 Dental root-canal instruments—Part 2: Enlargers" and "ANSI/ADA Specification No. 95, for Root canal enlargers".

DETAILED DESCRIPTION OF THE INVENTION

Figure 1:
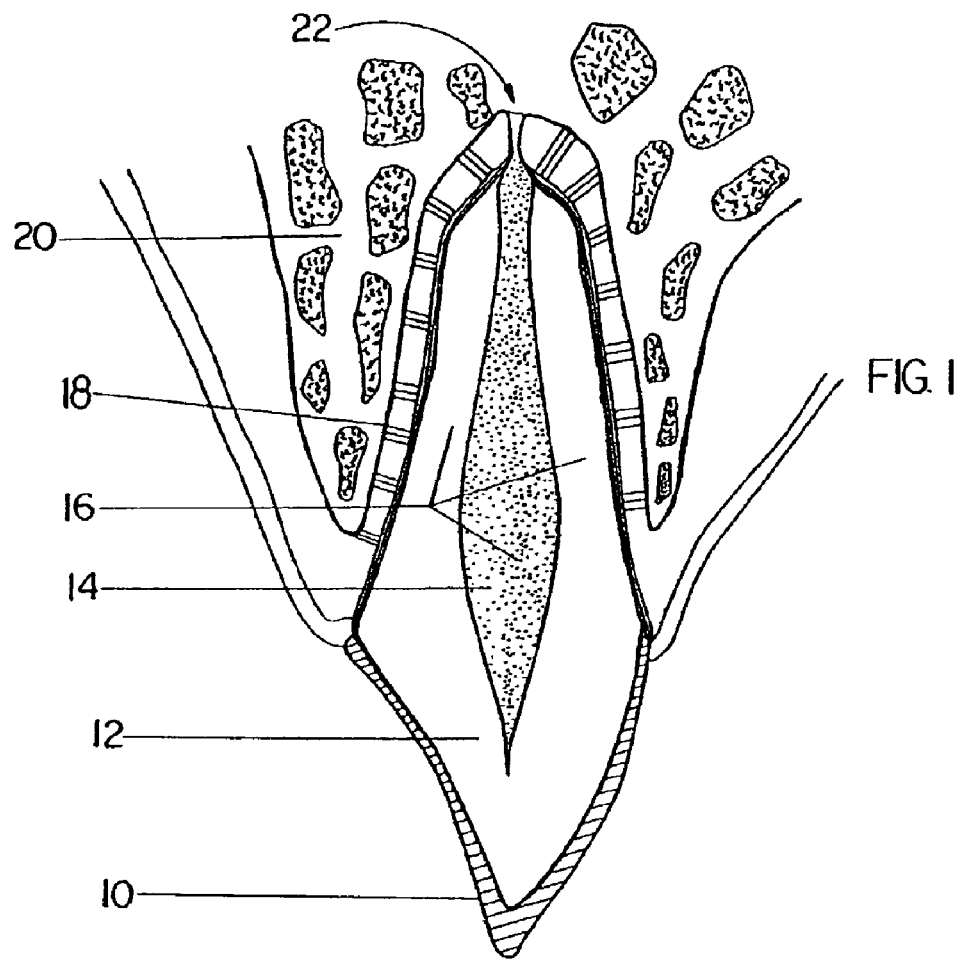
FIG. 1 is a cross-sectional view of a tooth.
Figure 2:
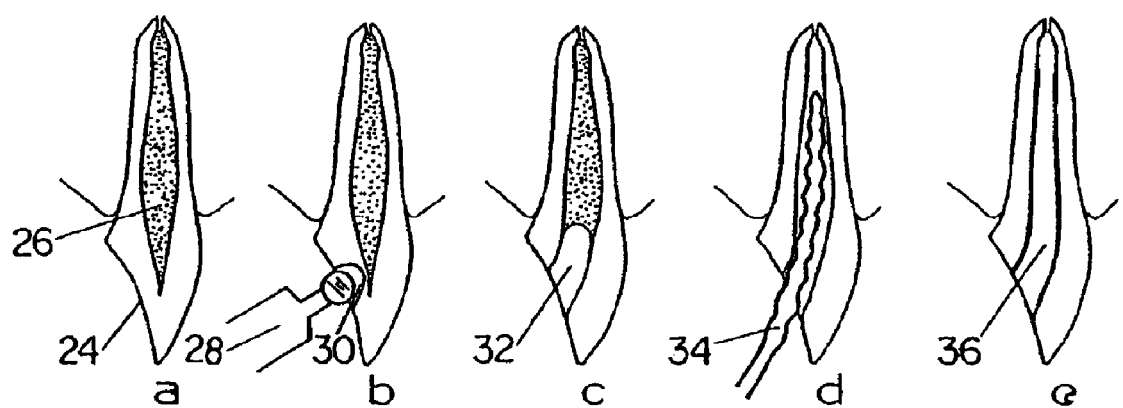
FIGS. 2a-2e represent a prior art procedure for preparing a tooth for endodontic restoration.

One embodiment of the invention provides an improved endodontic instrument for use in performing root canal therapy on a tooth. This embodiment of the invention is an endodontic instrument as shown in FIG. 1a that includes an elongate shank 42 mounted at its proximate end 47 to a handle 43. The shank 42 may be about 30 millimeters long. The proximate end 47 may have a diameter of about 0.5 to about 1.6 millimeters. The shank 42 may include calibrated depth markings 45 and further includes a distal end 48. The shank 42 includes two continuous helical flutes 51 as shown in FIG. 1b that extend along its lower portion. The flutes 51 define a cutting edge. A helical land 53 is positioned between axially adjacent flutes as shown in FIG. 1b.

The shank 42 comprises a titanium alloy, and is prepared by heat-treating the shank at a temperature above 25° C. in an atmosphere consisting essentially of a gas unreactive with the shank. Preferably, the temperature is from 400° C. up to but not equal to the melting point of the titanium alloy, and most preferably, the temperature is from 475° C. to 525° C. Preferably, the gas is selected from the group consisting of helium, neon, argon, krypton, xenon, and radon. Most preferably, the gas is argon. In one example embodiment, the shank is heat-treated for approximately 1 to 2 hours. In another example embodiment, the shank is heat-treated at 500° C. for 75 minutes. However, other temperatures are suitable as they are dependent on the time period selected for heat exposure.

The titanium alloy may be selected from alpha-titanium alloys, beta-titanium alloys, alpha-beta-titanium alloys, and nickel-titanium alloys. Non-limiting examples of alpha-titanium alloys, beta-titanium alloys, alpha-beta-titanium alloys for use in this embodiment of the invention are: Ti-5Al-2.5Sn alpha alloy; Ti-5Al-2.5Sn-ELI (low $O_2$) alpha alloy; Ti-3Al-2.5V alpha alloy; Ti-5Al-5Zr-5Sn alpha alloy; Ti-6Al-2Cb-1Ta-0.8Mo alpha alloy; Ti-5Al-5Sn-2Zr-2Mo-0.25Si near alpha alloy; Ti-6Al-2Nb-1Ta-1Mo near alpha alloy; Ti-8Al-1Mo-1V near alpha alloy; Ti-6Al-2Sn-4Zr-2Mo near alpha alloy; Ti-6Al-2Sn-1.5Zr-1Mo-0.35Bi-0.1Si near alpha alloy; Ti-2.25-Al-11Sn-5Zr-1Mo-0.2Si near alpha alloy; Ti-3Al-2.5V alpha-beta alloy; Ti-10V-2Fe-3Al alpha-beta alloy; Ti-5Al-2Sn-2Zr-4Mo-4Cr alpha-beta alloy; Ti-6Al-2Sn-4Zr-6Mo alpha-beta alloy; Ti-4Al-4Mn alpha-beta alloy; Ti-6Al-2Sn-2Zr-2Mo-2Cr-0.25Si alpha-beta alloy; Ti-4Al-3Mo-1V alpha-beta alloy; Ti-6Al-2Sn-4Zr-6Mo alpha-beta alloy; Ti-11Sn-5Zr-2Al-1Mo alpha-beta alloy; Ti-6Al-4V alpha-beta alloy; Ti-6Al-4V-ELI (low $O_2$) alpha-beta alloy; Ti-6Al-6V-2Sn-0.75Cu alpha-beta alloy; Ti-7Al-4Mo alpha-beta alloy; Ti-6Al-2Sn-4Zr-2Mo alpha -beta alloy; Ti-5Al-1.5Fe-1.5Cr-1.5Mo alpha-beta alloy; Ti-8Mn alpha-beta alloy; Ti-8Mo-8V-2Fe-3Al beta alloy; Ti-11.5Mo-6Zr-4.5Sn beta alloy; Ti-3Al-8V-6Cr-4Mo-4Zr beta alloy; and Ti-3Al-13V-11Cr beta alloy (the numbers being percent by weight). An example, nickel-titanium alloy includes 54-57 weight percent nickel and 43-46 weight percent titanium. Preferably, the titanium alloy used for the shank includes 54-57 weight percent nickel and 43-46 weight percent titanium and is commercially available as Nitinol 55. Thus, most preferably, the shank consists essentially of 54-57 weight percent nickel and 43-46 weight percent titanium thereby avoiding the inclusion of elements that affect the superelastic properties of the alloy.

Another embodiment of the invention provides an improved endodontic instrument for use in performing root canal therapy on a tooth. This embodiment of the invention is an endodontic instrument as shown in FIG. 1a that includes an elongate shank 42 mounted at its proximate end 47 to a handle 43. The shank 42 may be about 30 millimeters long. The proximate end 47 may have a diameter of about 0.5 to about 1.6 millimeters. The shank 42 may include calibrated depth markings 45 and further includes a distal end 48. The shank 42 includes two continuous helical flutes 51 as shown in FIG. 1b, which extend along its lower portion. The flutes 51 define a cutting edge. A helical land 53 is positioned between axially adjacent flutes as shown in FIG. 1b. The endodontic instrument is fabricated solely from an alpha-titanium alloy, a beta-titanium alloy, or an alpha-beta-titanium alloy to avoid the problems associated with multiple alloy systems.

Non-limiting examples of alpha-titanium alloys, beta-titanium alloys, alpha-beta-titanium alloys for use in this embodiment of the invention are: Ti-5Al-2.5Sn alpha alloy; Ti-5Al-2.5Sn-ELI (low $O_2$) alpha alloy; Ti-3Al-2.5V alpha alloy; Ti-5Al-5Zr-5Sn alpha alloy; Ti-6Al-2Cb-1Ta-0.8Mo alpha alloy; Ti-5Al-5Sn-2Zr-2Mo-0.25Si near alpha alloy; Ti-6Al-2Nb-1Ta-1Mo near alpha alloy; Ti-8Al-1Mo-1V near alpha alloy; Ti-6Al-2Sn-4Zr-2Mo near alpha alloy; Ti-6Al-2Sn-1.5Zr-1Mo-0.35Bi-0.1Si near alpha alloy; Ti-2.25-Al-11Sn-5Zr-1Mo-0.2Si near alpha alloy; Ti-3Al-2.5V alpha-beta alloy; Ti-10V-2Fe-3Al alpha-beta alloy; Ti-5Al-2Sn-2Zr-4Mo-4Cr alpha-beta alloy; Ti-6Al-2Sn-4Zr-6Mo alpha-beta alloy; Ti-4Al-4Mn alpha-beta alloy; Ti-6Al-2Sn-2Zr-2Mo-2Cr-0.25Si alpha-beta alloy; Ti-4Al-3Mo-1V alpha-beta alloy; Ti-6Al-2Sn-4Zr-6Mo alpha-beta alloy; Ti-11Sn-5Zr-2A-1Mo alpha-beta alloy; Ti-6Al-4V alpha-beta alloy; Ti-6Al-4V-ELI (low $O_2$) alpha-beta alloy; Ti-6Al-6V-2Sn-0.75Cu alpha-beta alloy; Ti-7Al-4Mo alpha-beta alloy; Ti-6Al-2Sn-4Zr-2Mo alpha-beta alloy; Ti-5Al-1.5Fe-1.5Cr-1.5Mo alpha-beta alloy; Ti-8Mn alpha-beta alloy; Ti-8Mo-8V-2Fe-3Al beta alloy; Ti-11.5Mo-6Zr-4.5Sn beta alloy; Ti-3Al-8V-6Cr-4Mo-4Zr beta alloy; and Ti-3Al-13V-11Cr beta alloy (the numbers being percent by weight). These alloys of titanium include phase stabilizing amounts of a metal selected from molybdenum, tin, bismuth, tantalum, vanadium, zirconium, niobium, chromium, cobalt, nickel, manganese, iron, aluminum and lanthanum. An endodontic instrument according to this embodiment of the invention has improved sharpness, cutting ability, and instrument longevity compared to instruments fabricated from untreated nickel-titanium. Alpha-titanium, beta-titanium and alpha-beta-titanium are superior because they are harder and hence will hold an edge better and still maintain near the flexibility of nickel-titanium to negotiate curved canals. These alpha-titanium, beta-titanium and alpha-beta-titanium instruments may include medical, dental and endodontic instruments (both hand and engine driven), cutting burs (drills), and enlarging instruments including hand, mechanical and rotary.

Present medical and dental practice entails cutting of hard tissues such as bone or teeth with instruments manufactured of carbide steel, stainless steel and nickel-titanium. Present endodontic practice entails the preparation, cleaning, and shaping of root canals in teeth utilizing carbide steel, stainless steel and nickel-titanium instruments for hand, mechanical and rotary applications. This version of the invention would use an alpha-titanium alloy, a beta-titanium alloy, or an alpha-beta-titanium alloy to fabricate these instruments. It may be coated (as described below) or uncoated. Today a growing number of physicians and dentists (endodontists) are utilizing engine driven drills and files with various names and applications. This aspect of the present invention pertains to the fabrication of these cutting instruments such as drills and files solely from an alpha-titanium alloy, a beta-titanium alloy, or an alpha-beta-titanium alloy to produce a sharper cutting edge that should provide for better cutting or a smooth finished surface. This includes instrumentation that will facilitate the cleaning and sealing of the root canal system. In addition, a coating or heat-treatment may relieve stress in the instrument to allow it to withstand more torque, rotate through a larger angle of deflection, change the handling properties, or visually exhibit a near failure of the instrument. This aspect of the invention relates to all drills, burs, files, and instruments used in medicine and dentistry.

In another aspect, the present invention provides for coating and optionally thereafter heat-treating dental and medical instruments including the coatings to maintain and/or improve their sharpness, cutting ability, and/or instrument longevity. Such an instrument may be manufactured from nickel-titanium, an alpha-titanium alloy, a beta-titanium alloy, or an alpha-beta-titanium alloy, stainless steel, carbide steel, as well as other materials. These instruments may be electropolished before or after coating or heat-treating. These instruments will include medical, dental and endodontic instruments (both hand and engine driven), cutting burs (drills), and enlarging instruments including hand, mechanical and rotary.

The coating processes may include but not limited to the following processes: composite electroless plating (see, e.g., U.S. Pat. Nos. 4,820,547; 4,997,686; 5,145,517; 5,300,330; 5,863,616; and 6,306,466); chemical vapor deposition (see, e.g., U.S. Pat. No. 4,814,294); microwave deposition (see, e.g., U.S. Pat. No. 4,859,493); laser ablation process (see, e.g., U.S. Pat. No. 5,299,937); ion beam assisted deposition (see, e.g., U.S. Pat. No. 5,725,573); physical vapor deposition (see, e.g., U.S. Pat. Nos. 4,670,024, 4,776,863, 4,984,940, and 5,545,490); Molybdenum Disulfide Coating ($MoS_2$) (see, e.g., U.S. Pat. No. 5,037,516 or SAE Standard AMS2526); electropolishing; coatings including titanium nitride and titanium aluminum nitride commercially available under the trademark Firex™; coatings such as titanium nitride (TiN), titanium carbonitride (TiCN), titanium aluminum nitride (TiAlN), aluminum titanium nitride (AlTiN); or multiple coatings or combinations of coatings.

As detailed above, present medical and dental practice entails cutting of hard tissues such as bone or teeth with instruments manufactured of carbide steel, stainless steel and nickel-titanium. Present endodontic practice entails the preparation, cleaning, and shaping of root canals in teeth utilizing carbide steel, stainless steel and nickel-titanium. These can be manufactured as hand, mechanical and rotary instruments. Today a growing number of physicians and dentists (endodontists) are utilizing engine driven drills and files with various names and applications. This aspect of the present invention pertains to the application of coatings and optionally heat-treatment to cutting instruments such as drills and files to produce a sharper cutting edge and a higher resistance to heat degradation that should provide for better cutting, a smooth surface and/or different metallurgical properties than the material from which it was manufactured. This includes instrumentation that will facilitate the cleaning and sealing of the root canal system. In addition, a heat-treatment separately applied or as utilized in the coating process may relieve stress in the instrument which should allow for more instrument longevity by the ability to withstand more torque, rotate through a larger angle of deflection, change the handling properties, remove shape memory or visually exhibit a near failure of the instrument. This aspect of the invention relates to all drills, burs, files, and instruments used in medicine and dentistry.

One example process of this aspect of the present invention for such instruments is a titanium nitride coating. This coating process is done with physical vapor deposition with an inherent heat-treatment. Another process is a multilayer process utilizing a titanium nitride coating and then a titanium aluminum nitride coating. This last coating process is commercially available under the trademark FIREX™.

Another example process of this aspect of the present invention for such instruments is a metal or metal alloy coating incorporating particulate matter. One process to produce such a coating to an instrument includes contacting the surface of the instrument with a stable electroless metallizing bath comprising a metal salt, an electroless reducing agent, a complexing agent, an electroless plating stabilizer, a quantity of particulate matter which is essentially insoluble or sparingly soluble in the metallizing bath, and a particulate matter stabilizer, and maintaining the particulate matter in suspension in the metallizing bath during the metallizing of the instrument for a time sufficient to produce a metallic coating with the particulate matter dispersed.

EXAMPLES

The following Examples have been presented in order to further illustrate the invention and are not intended to limit the invention in any way.

Example 1

Thirty ISO size SX files, thirty ISO size S1 files, thirty ISO size S2 files, thirty ISO size F1 files, thirty ISO size F2 files and thirty ISO size F3 files were used in a study of torsion ($M_t$) reported in g·cm performed in accordance with "ISO Standard 3630-1 Dentistry—Root-canal instruments—Part 1: General requirements" and "ANSI/ADA Specification No. 28, Endodontic files and reamers". The results are shown in FIG. 3. The files were made from a titanium alloy comprising 54-57 weight percent nickel and 43-46 weight percent titanium, and included an elongate shank having a cutting edge extending from a distal end of the shank along an axial length of the shank. Ten of each ISO size were untreated (Control) files. Ten of each ISO size were heat-treated in a furnace in an argon atmosphere at 500° C. for 75 minutes. These are labeled "TT" in FIG. 3. Ten of each ISO size were coated with titanium nitride using physical vapor deposition with an inherent heat-treatment. These are labeled "Ti—N" in FIG. 3. $M_t$ was determined for each of the thirty files in each size, and the mean and standard deviation for each group (Control, TT, Ti—N) of ten files were calculated. The ten files in all but one size that were heat-treated in a furnace in an argon atmosphere at 500° C. for 75 minutes showed the best result with the highest $M_t$.

Example 2

Thirty ISO size SX files, thirty ISO size S1 files, thirty ISO size S2 files, thirty ISO size F1 files, thirty ISO size F2 files and thirty ISO size F3 files were used in a study of torsion ($A_t$) reported in degrees of deflection performed in accordance with "ISO Standard 3630-1 Dentistry—Root-canal instruments—Part 1: General requirements" and "ANSI/ADA Specification No. 28, Endodontic files and reamers". The results are shown in FIG. 4. The files were made from a titanium alloy comprising 54-57 weight percent nickel and 43-46 weight percent titanium, and included an elongate shank having a cutting edge extending from a distal end of the shank along an axial length of the shank. Ten of each ISO size were untreated (Control) files. Ten of each ISO size were heat-treated in a furnace in an argon atmosphere at 500° C. for 75 minutes. These are labeled "TT" in FIG. 4. Ten of each ISO size were coated with titanium nitride using physical vapor deposition with an inherent heat-treatment. These are labeled "Ti—N" in FIG. 4. $A_t$ was determined for each of the thirty files in each size, and the mean and standard deviation for each group (Control, TT, Ti—N) of ten files were calculated. The ten files in each size that were heat-treated in a furnace in an argon atmosphere at 500° C. for 75 minutes showed the best results with the highest $A_t$.

Example 3

Thirty ISO size SX files, thirty ISO size S1 files, thirty ISO size S2 files, thirty ISO size F1 files, thirty ISO size F2 files and thirty ISO size F3 files were used in a study of maximum torque at 45° of flexion ($M_f$) reported in g·cm performed in accordance with "ISO Standard 3630-1 Dentistry—Root-canal instruments—Part 1: General requirements" and "ANSI/ADA Specification No. 28, Endodontic files and reamers". The shank is held in a torque meter, flexed at an angle of 45°, and then torque is measured. The results are shown in FIG. 5. The files were made from a titanium alloy comprising 54-57 weight percent nickel and 43-46 weight percent titanium, and included an elongate shank having a cutting edge extending from a distal end of the shank along an axial length of the shank. Ten of each ISO size were untreated (Control) files. Ten of each ISO size were heat-treated in a furnace in an argon atmosphere at 500° C. for 75 minutes. These are labeled "TT" in FIG. 5. Ten of each ISO size were coated with titanium nitride using physical vapor deposition with an inherent heat-treatment. These are labeled "Ti—N" in FIG. 5. Mf was determined for each of the thirty files in each size, and the mean and standard deviation for each group (Control, TT, Ti—N) of ten files were calculated. It can be seen that the heat-treated files in each size impart less torque when bent and appear to have higher flexibility than untreated (control) files.

Example 4

Thirty ISO size SX files, thirty ISO size S1 files, thirty ISO size S2 files, thirty ISO size F1 files, thirty ISO size F2 files and thirty ISO size F3 files were used in a study of angle of permanent deformation after the flexion test (ADP) reported in degrees of deflection performed in accordance with "ISO Standard 3630-1 Dentistry—Root-canal instruments—Part 1: General requirements" and "ANSI/ADA Specification No. 28, Endodontic files and reamers". The results are shown in FIG. 6. The files were made from a titanium alloy comprising 54-57 weight percent nickel and 43-46 weight percent titanium, and included an elongate shank having a cutting edge extending from a distal end of the shank along an axial length of the shank. Ten of each ISO size were untreated (Control) files. Ten of each ISO size were heat-treated in a furnace in an argon atmosphere at 500° C. for 75 minutes. These are labeled "TT" in FIG. 6. Ten of each ISO size were coated with titanium nitride using physical vapor deposition with an inherent heat-treatment. These are labeled "Ti—N" in FIG. 6. ADP was determined for each of the thirty files in each size, and the mean and standard deviation for each group (Control, TT, Ti—N) of ten files were calculated. The ten files in each size that were heat-treated in a furnace in an argon atmosphere at 500° C. for 75 minutes showed the highest ADP. Thus, the heat-treated files significantly maintain the acquired (test deformed) shape rather than the shape memory exhibited in the untreated control (nickel-titanium instruments).

Example 5

Six groups of thirty ISO size SX, S1, S2, F1, F2 and F3 files were used in a study of the fatigue reported in cycles (revolutions) to failure performed in accordance with the "ISO Standard 3630-2 Dental root-canal instruments—Part 2: Enlargers" and "ANSI/ADA Specification No. 95, for Root canal enlargers". The results are shown in FIG. 7. The files were made from a titanium alloy comprising 54-57 weight percent nickel and 43-46 weight percent titanium, and included an elongate shank having a cutting edge extending from a distal end of the shank along an axial length of the shank. Ten files of each ISO size were untreated (Control)

files. Ten files of each ISO size were heat-treated in a furnace in an argon atmosphere at 500° C. for 75 minutes. These are labeled "TT" in FIG. 7. Ten files of each ISO size were coated with titanium nitride using physical vapor deposition with an inherent heat-treatment. These are labeled "Ti—N" in FIG. 7. Fatigue cycles were determined for each of the files in each size, and the mean and standard deviation for each group (Control, TT, Ti—N) of the six file sizes were calculated. The ten files in all but one size that were heat-treated in a furnace in an argon atmosphere at 500° C. for 75 minutes showed the best result with the highest fatigue cycles (revolutions) to failure.

The Examples show that heat-treated files (TT) exhibit higher resistance to torsion breakage, can withstand increased strain, have higher flexibility, have increased fatigue life and maintain any acquired shape upon fracture better when compared to untreated (Control) files. Thus, the invention provides medical and dental instruments, and particularly endodontic instruments, such as drills, burs and files, that have high resistance to torsion breakage, maintain shape upon fracture, can withstand increased strain, and can hold sharp cutting edges such that the instruments overcome the problems encountered when cleaning and enlarging a curved root canal.

Although the present invention has been described in considerable detail with reference to certain embodiments, one skilled in the art will appreciate that the present invention can be practiced by other than the described embodiments, which have been presented for purposes of illustration and not of limitation. For example, while the present invention finds particular utility in the field of endodontic instruments, the invention is also useful in other medical and dental instruments used in creating or enlarging an opening. Therefore, the scope of the appended claims should not be limited to the description of the embodiments contained herein.

What is claimed is:

1. An endodontic instrument for use in performing root can therapy on a tooth, the instrument comprising:
   an elongate shank having a cutting edge extending from a distal end of the shank along an axial length of the shank, the instrument being a size in accordance with ISO Standard 3630-1,
   wherein the shank comprises a titanium alloy, and
   wherein the instrument is prepared by heat-treating the entire shank for a time period at a single temperature in an atmosphere consisting essentially of a gas unreactive with the shank,
   wherein the temperature is from 400° C. up to but not equal to the melting point of the titanium alloy, and
   wherein the heat-treated instrument has an angle greater than 10 degrees of permanent deformation after torque at 45° of flexion tested in accordance with ISO Standard 3630-1.

2. The instrument of claim 1 wherein:
   the gas is selected from the group consisting of helium, neon, argon, krypton, xenon, and radon.

3. The instrument of claim 1 wherein:
   the temperature is from 475° C. to 525° C.

4. The instrument of claim 1 wherein:
   the instrument is heat-treated for 1 to 2 hours.

5. The instrument of claim 1 wherein:
   the titanium alloy is selected from alpha-titanium alloys, beta-titanium alloys, alpha-beta-titanium alloys, and nickel-titanium alloys.

6. The instrument of claim 1 wherein:
   the titanium alloy comprises 54-57 weight percent nickel and 43-46 weight percent titanium.

7. The instrument of claim 1 wherein:
   the titanium alloy comprises 54-57 weight percent nickel and 43-46 weight percent titanium,
   the gas is selected from the group consisting of helium, neon, argon, krypton, xenon, and radon,
   the temperature is from 475° C. to 525° C., and
   the instrument is heat-treated for 1 to 2 hours.

8. The instrument of claim 1 wherein:
   the shank consists essentially of a titanium alloy comprising 54-57 weight percent nickel and 43-46 weight percent titanium,
   the gas is argon,
   the temperature is 500° C., and
   the instrument is heat-treated for 1 to 2 hours.

9. The instrument of claim 1 wherein:
   the cutting edge is formed by helical flutes in the shank.

10. The instrument of claim 1 wherein:
    the shank has a diameter of 0.5 to 1.6 millimeters.

11. The instrument of claim 1 wherein:
    the temperature is from 400° C. to 525° C.

12. An endodontic instrument for use in performing root canal therapy on a tooth, the instrument comprising:
    an elongate shank having helical flutes defining a cutting edge extending from a distal end of the shank along an axial length of the shank, the instrument being a size in accordance with ISO Standard 3630-1,
    wherein the shank consists essentially of a titanium alloy comprising 54-57 weight percent nickel and 43-46 weight percent titanium, and
    wherein the instrument is prepared by heat-treating the entire shank at a temperature from 475° C. to 525° C. in an atmosphere consisting essentially of a gas unreactive with the shank, and
    wherein the heat-treated instrument has an angle greater than 10 degrees of permanent deformation after torque at 45° of flexion tested in accordance with ISO Standard 3630-1.

13. The instrument of claim 12 wherein:
    the shank has a diameter of 0.5 to 16 millimeters.

14. A method for creating or enlarging an opening in a tooth of a patient undergoing root canal therapy, the method comprising:
    creating or enlarging the opening using an instrument according to claim 1.

15. A method for creating or enlarging an opening in a tooth of a patient undergoing root canal therapy, the method comprising:
    creating or enlarging the opening using an instrument according to claim 12.

16. An endodontic instrument for use in performing root canal therapy on a tooth, the instrument comprising:
    an elongate shank having a cutting edge extending from a distal end of the shank along an axial length of the shank, wherein the shank comprises a titanium alloy, and wherein the instrument has a size in accordance with ISO Standard 3630-1, and wherein the instrument is prepared by heat-treating the entire shank for a time period at a single temperature in an atmosphere consisting essentially of a gas unreactive with the shank, wherein the temperature is from 400° C. up to but not equal to the melting point of the titanium ahoy, and wherein the heat-treated instrument has an angle greater than 10 degrees of permanent deformation after torque at 45° of flexion tested in accordance with ISO Standard 3630-1.

17. The instrument of claim 16 wherein:
the temperature is from 400° C. to 525° C.

18. The instrument of claim 16 wherein:
the temperature is from 475° C. to 525° C.

* * * * *

UNITED STATES PATENT AND TRADEMARK OFFICE
CERTIFICATE OF CORRECTION

PATENT NO.         : 8,062,033 B2
APPLICATION NO.    : 11/628933
DATED              : November 22, 2011
INVENTOR(S)        : Neill H. Luebke It is certified that error appears in the above-identified patent and that said Letters Patent is hereby corrected as shown below:

In the Claims

Column 9, line 42 "root can" should read --root canal--

Column 11, line 9 "ahoy" should read --alloy--

Signed and Sealed this
Thirty-first Day of December, 2013

Margaret A. Focarino
*Commissioner for Patents of the United States Patent and Trademark Office*